United States Patent [19]

Simon et al.

[11] Patent Number: 4,567,036

[45] Date of Patent: Jan. 28, 1986

[54] CHEMOTHERAPEUTIC METHOD FOR TREATING PERIODONTAL DISEASE, AND COMPOSITION THEREFORE

[76] Inventors: Gilbert I. Simon, 111 Midland Ave., Bronxville, N.Y. 10708; Roy T. Witkin, 23 Broadview Rd., Westport, Conn. 06880

[21] Appl. No.: 708,688

[22] Filed: Mar. 6, 1985

Related U.S. Application Data

[60] Division of Ser. No. 565,661, Dec. 30, 1983, Pat. No. 4,521,403, which is a continuation-in-part of Ser. No. 459,525, Jan. 20, 1983, abandoned, which is a continuation-in-part of Ser. No. 145,590, May 1, 1980, abandoned.

[51] Int. Cl.$^4$ .................. A61K 7/20; A61K 31/79; A61K 33/18; A61K 31/755
[52] U.S. Cl. .................................. 424/51; 424/49; 424/53; 424/80; 424/150
[58] Field of Search .................. 424/51, 53, 80, 150

[56] References Cited

U.S. PATENT DOCUMENTS

| | | | |
|---|---|---|---|
| 975,354 | 11/1910 | Gruter et al. | 424/53 |
| 1,018,240 | 2/1912 | Von Foregger | 424/53 |
| 2,090,437 | 8/1937 | Woldman | 424/53 |
| 2,218,172 | 10/1934 | Kokatnur | 167/93 |
| 2,275,979 | 3/1942 | Molnar | 424/51 |
| 2,501,145 | 3/1950 | Smith | 424/53 |
| 2,706,701 | 4/1955 | Beller et al. | 167/70 |
| 2,739,922 | 3/1956 | Shelanski | 424/150 |
| 2,840,510 | 6/1958 | Katz et al. | 424/51 |
| 3,136,755 | 6/1964 | Grosser et al. | 424/51 |
| 3,936,385 | 2/1976 | Cheng | 252/99 |
| 3,966,090 | 6/1976 | Prussin et al. | 424/43 |
| 3,996,126 | 12/1976 | Rasmussen | 204/271 |
| 4,113,857 | 9/1978 | Shetty | 424/150 |
| 4,151,275 | 4/1979 | Cantor et al. | 424/150 |
| 4,183,916 | 1/1980 | Rodon | 424/54 |
| 4,226,851 | 10/1980 | Sompayrac | 424/53 |
| 4,302,441 | 11/1981 | Muhlemann et al. | 424/53 |
| 4,401,651 | 8/1983 | Knutson | 424/80 |
| 4,521,403 | 6/1985 | Simon et al. | 424/51 |

FOREIGN PATENT DOCUMENTS

| | | |
|---|---|---|
| 2355010 | 5/1975 | Fed. Rep. of Germany . |
| 2438594 | 2/1976 | Fed. Rep. of Germany . |
| 421962 | 12/1934 | United Kingdom . |
| 604350 | 7/1948 | United Kingdom . |

OTHER PUBLICATIONS

Federal Register, 5/82, p. 22875.
Zinner et al., OS, OM & OP 11/61, p. 1378.
JADA, vol. 105, 7/82, p. 28.
Rhodes et al., NTIS 12/78.
Ferguson et al., British Dental Journal 1978, 144, 14.
Prevention 11/83, Maser Article, pp. 84–88.
Dental Abstracts 24, (1979), pp. 152–153.
Dental Abstracts 25, (1980), p. 434.
Chem. Abstracts, vol. 91, Item 11062b, (1979).
IADR Abstracts (1982), Item, 854.
Elion et al., J. Biol. Chem. 208, 477–488, (1954).
Kerry et al., Journal of Antimocrobial Chemotherapy (1975) 1, 417–427.
Randall et al., Brenman et al., J. Periodont, 45: 866–869, 870, 872, Dec. 1974, Local Degerming with Povidone–Iodine I. Prior to Dental Prophylaxis II. Prior to Gingivectomy.
Scopp et al., J.A.D.A. 83: 1294–1296, Dec. 1971, Gingival Degerming by Povidone–Iodine Irrigation.
Shelanski et al., J. Int. Coll. Surgeons 25: 727–734, Jun. 1956, PVP–Iodine: History, Toxicity and Therapeutic Uses.

(List continued on next page.)

*Primary Examiner*—Shep K. Rose
*Attorney, Agent, or Firm*—Jacobs & Jacobs

[57] ABSTRACT

A method is described for controlling and treating periodontal diseases by applying to the teeth and periodontium an oral lavage comprised of an aqueous solution of hydrogen peroxide and a povidone-iodine complex.

13 Claims, 4 Drawing Figures

OTHER PUBLICATIONS

Rundegren et al., Scand. J. Dent. Res. 81: 543–547, (1973), In Vivo and In Vitro Studies on a New Peroxide-Containing Toothpaste.

Knighton, J. Dent. Res. 19: 429–439, Oct. 1940, The Effect of Oxidizing Agents on Certain Non-Spore-Forming Anaerobes.

Chem. Abstract 90th 12346p (1979) of Gluck German Offen. 2,718,385, Nov. 2, 1978.

Moller, Microbiological Examination of Root Canals and Periapical Tissues of Human Teeth, p. 30.

Dannenburg et al., Amer. J. Hosp. Pharmacy 35: 528 May 1978, Betadine-Hydrogen Peroxide Irrigation Solution Incompatibility.

A.D.A. Accepted Dental Therapeutics 38th ed. Sep. 1979, (RK 701A3), American Dental Assoc., Chicago, IL pp. 223–224, 226–227, 236, 278, 281, 284, 339–347.

Figure 4

CHEMOTHERAPEUTIC METHOD FOR TREATING PERIODONTAL DISEASE, AND COMPOSITION THEREFORE

RELATED CASES

This application is a division of application Ser. No. 565,661 filed Dec. 30, 1983, now U.S. Pat. No. 4,521,403 issued June 4, 1985, which is a continuation-in-part of prior co-pending application Ser. No. 459,525 filed Jan. 20, 1983, which is a continuation-in-part of prior co-pending application Ser. No. 145,590 filed May 1, 1980, both now abandoned.

BACKGROUND OF THE INVENTION

This invention relates to an improved method of controlling and treating diseases of the teeth and periodontium by applying an oral lavage thereto.

Periodontal disease is one of the world's most prevalent diseases and is the primary cause of tooth loss in adults throughout the world.

After teeth are cleaned, they soon become coated with "plaque" which is comprised of organic deposits from saliva, desquamated epithelial cells and masses of oral microorganisms which not only cause caries in the teeth, but are also believed to be the cause of chronic disease of the periodontal tissues. The primary techniques presently employed for removing plaque and the bacteria contained therein surrounding the teeth is (a) mechanical means of scaling or root planing the teeth by a dentist or oral hygienist or (b) flossing the teeth by the patient.

The specific identity of the bacteria in the mouth which causes periodontal diseases may vary. Bacteria which have been implicated as causing periodontal disease include *Actinomyces viscosus, Bacteroides intermedius,* and *Bacteroides gingivalis.* Although certain chemicals such as alcohol, iodine and the like have been used in the preparation of oral lavages or antiseptics to control the periodontal bacteria, none of these oral lavages have been found to be suffiently effective in controlling the periodontal bacteria and hence the disease.

Recent research has shown that periodontal disease can be controlled and treated by the use of certain topically applied antimicrobial agents. Chlorhexidine has, for example, been proven effective in treating periodontal disease. However, the Federal Drug Administration has not permitted these topical agents to be marketed in the United States because of toxicity or cosmetic problems, even though the agents have been proven to be effective in the treatment of periodontal disease. There is a need for an oral lavage which will treat and control periodontal disease and which is cosmetically acceptable and free of toxicity problems.

Recently, Dr. Paul H. Keyes and Associates proposed a method for controlling periodontal disease by daily brushing of the teeth and gums with a dentifrice comprised of a thick mixture of baking soda moistened with a 3 percent solution of hydrogen peroxide. Following brushing of the teeth and massaging of the gums with this paste, the mouth is rinsed with salt water. Although this technique has received extensive publicity and has been used as a remedy by many individuals, its claimed benefits have not been substantiated or reproduced by controlled experimentation. In addition, the high sodium concentration of ingredients used in this technique may be undesirable for use by individuals suffering from hypertension.

There is a need at the present time for an oral lavage which will control the growth of microorganism which cause periodontal disease, thereby reducing the loss of teeth.

It is a primary object of this invention to provide such an improved oral lavage for use in controlling periodontal disease in the mouth.

It is a further object of this invention to provide an improved oral lavage which is substantially free of sodium for use in controlling the growth of bacteria which cause periodontal disease in the mouth.

Still another object of the invention is to provide an improved method of controlling and treating periodontal disease with an oral lavage.

These and other objects of the invention will be apparent from the following detailed description thereof.

It has now been discovered that the foregoing objects of this invention are accomplished in a method of controlling disease of the teeth and periodontium which comprises applying to said teeth and periodontium an oral lavage comprised of an aqueous solution of hydrogen peroxide and povidone iodine complex wherein said oral lavage contains from about 0.5 to about 10 percent by weight of hydrogen peroxide and from about 0.05 to about 2.0 percent by weight of iodine derived from said complex.

More in detail, the oral lavage used in the method of this invention is prepared by admixing an aqueous solution of hydrogen peroxide with a povidone-iodine complex. Hydrogen peroxide is available commercially as an aqueous solution in a wide variety of concentrations ranging from about 3 to about 30 percent.

Povidone iodine complex is also available in a wide variety of concentrations ranging from about 0.5 to about 10.0 percent. If desired, sufficient solid povidone iodine complex may be added directly to the aqueous hydrogen peroxide solution to obtain the desired iodine concentration. In addition, solid povidone iodine complex may be used to first form an aqueous solution or an aqueous alcoholic solution of the complex before admixing with the hydrogen peroxide solution to the desired concentration level. The povidone iodine complex is a complex of iodine with 1-vinyl-2-pyrrolidinone polymers, as described in U.S. Pat. Nos. 2,706,702; 2,876,532; and 2,900,305. The term "iodine by weight derived from the povidone iodine complex" as used throughout the description and claims is that amount of iodine present in the form of titratable diatomic iodine using sodium thiosulfate. This is also identified as "$I_2$", particularly in the examples, while the povidone iodine complex is identified as "$PVP-I_2$".

Both the hydrogen peroxide and povidone iodine complex are soluble in water which serves as a carrier and medium for their interaction when admixed in accordance with this invention. The hydrogen peroxide and povidone iodine complex are admixed in sufficient proportion to provide a mixture which serves as an oral lavage having a concentration of hygroden peroxide in the range of from about 0.5 to about 10 percent, and preferably from about 1.0 and about 4.0 percent, by weight of the mixture.

Sufficient povidone iodine complex in one of the aforesaid forms is admixed to provide a mixture useful as an oral lavage which contains from about 0.05 to about 2.0 percent, and preferably from about 0.12 and about 0.5 percent iodine by weight derived from the povidone iodine complex. The povidone iodine complex when in solution form may also contain flavoring agents as well as buffering agents to maintain the proper pH to enhance the stability of the complex over an acceptable period of time while stored and not in use.

The oral lavage of this invention should be used as soon as possible after the hydrogen peroxide solution is admixed with the povidone iodine complex in the above-defined proportions. The resulting oral lavage may be applied to teeth, gums and other teeth supporting structures by rinsing the mouth in the same manner as with a conventional mouthwash. While the intensity of the periodontal disease may vary with the individual, effective treatment has been observed when the oral lavage is retained in the mouth for about 20 to about 40 seconds. Rinsing the mouth in this manner is preferably effected from about three to about seven times per week. However, the frequency of the application may be varied for each individual.

Highly improved results are achieved if the solution is also infused by the dentist to the periodontium and teeth by an ordinary irrigating device known to be conventional in the dental art. Applying the oral lavage between the gums and teeth, preferably below the gum line, by an irrigating device has been found to be an effective means of controlling periodontal disease.

It has been found that when the weight ratio of hydrogen peroxide to iodine derived from the povidone iodine complex in the oral lavage is in the range from about 0.25:1 to about 200:1 and preferably from about 2:1 to about 40:1, the oral lavage is very effective in controlling diseases which have been implicated as causing periodontal disease. Without being bound by theory, it is believed that when the oral lavage containing hydrogen perioxide is present in the mouth, there is a greater amount of iodine released from the complex. This action insures a greater degree of germicidal activity by the iodine itself, as well as by the accompanying oxygen liberated from the hydrogen perioxide component of the oral lavage. This not only increases the germicidal potential of the iodine itself, but also insures that a broad spectrum of periodontal bacteria may be destroyed by the oral lavage of this invention in a more effective and efficient manner when compared to the oral lavages of the prior art.

In practice, the oral lavage of this invention functions to improve anticepsis on the surface of the teeth and gums. This action insures that more effective protection is maintained in the interim between normal periodic visits for professional dental care. In many cases, as a result of such everyday self-care by the individual himself, the professional care required during such visits is minimized.

In carrying out the method of this invention, the above described ingredients for preparing the oral lavage in the above described proportions are provided in separate packages, each package containing one of the described ingredients in the measured amounts desired. Just prior to use, each of the packages is opened, the contents are admixed in a single vessel and applied to the teeth and gums. In the present state of the packaging technology, it is possible to package each liquid ingredient in the desired amounts in a single segmented container or package. Each of the separate compartments may be manually broken, and the measured ingredients may be admixed within the package and supplied to the teeth and gums as an oral lavage. Alternatively, the container or package can be separated by a frangible barrier therebetween to form the containers, one for each of the components of the oral lavage. When use is desired, the barrier may be easily broken and both ingredients are admixed within the container and then applied to the mouth as an oral lavage.

The oral lavage of this invention when prepared and used as described, provides an unexpectedly improved cleansing effect upon the gums and surfaces of teeth, thereby reducing the broad spectrum of aerobic and anaerobic microorganisms on such surfaces.

Some people, more than others, have a greater propensity for bacterial-caused diseases of the mouth, teeth and periodontium. The use of the oral lavage herein described by these people in particular is very advantageous. The protection achieved by periodic visits for ordinary professional care by these people is substantially enhanced in the interim periods by frequent use of the oral lavage of this invention.

In some cases, the necessity for the application of restoratory and reconstructive procedures is substantially reduced with regular application of the oral lavage of this invention. Evidence of other oral diseases is also substantially decreased due to the interfunctional activity of each of the components of the oral lavage of this invention.

Having thus described the invention, the following examples are presented to illustrate the invention more fully. All parts and percentages are by weight unless otherwise specified.

EXAMPLE 1

An oral lavage of this invention was prepared by admixing equal volumes of 3% aqueous hydrogen peroxide solution and Pharmadine brand of providone iodine complex containing 1% by weight of titratable iodine. The resulting mixture contained 1.5% by weight of hydrogen peroxide and 0.5% by weight of iodine derived from the providone iodine complex. Pharmadine is a an aqueous alcoholic providone iodine solution containing about 10% by weight of providone iodine complex.

Three paper discs were placed on each of four agar plates approximately equidistant from each other. In each plate, a 25 $\mu$l aliquot of the aforesaid mixture was applied to the first paper disc. In addition, a 25 $\mu$l aliquot of the hydrogen peroxide solution only was applied to a second paper disc in each plate, and a 25 $\mu$l aliquot of the povidone iodine solution only was added to the third paper disc in each plate. Each disc was exposed for a period of five minutes to a membrane lawn of Actinomyces viscosus, one of the bacteria recognized as being implicated in causing periodontal disease in humans. After removing the paper discs, each lawn was placed on a nutrient agar plate containing tetraphenyl tetrazolium chloride (TTC) as an indicator of viable cells. After 48 hours of incubation, the plates were observed.

Three of the four plates showed that the 3% solution of hydrogen peroxide had little or no effect upon the bacteria, while the povidone iodine solution (1% $I_2$) had only a partial cidal effect. In contrast, the hydrogen peroxide-povidone iodine mixture of this invention, having an $H_2O_2$ concentration of 1.5% and an $I_2$ concentration of 0.5%, was completely cidal to the bacteria.

These results demonstrated an unexpected improvement by the oral lavage of this invention in the antimicrobial activity against *Actinomyces viscosus,* when compared to the individual components alone. The cidal effect of Applicants' mixture was synergistic since it exceeded the sum of individual components.

EXAMPLES 2-7

In another series of tests, six-¼ inch diameter filter paper discs were placed in spaced apart position on each of said nutrient agar plates. The discs, numbered 1-6, were placed on each plate and were saturated with 25 microliters per disc of one of the following solutions:

| Disc | Solution |
|---|---|
| 1 | an aqueous solution of povidone iodine containing MBC concentration of iodine |
| 2 | an aqueous solution of hydrogen peroxide containing MBC concentration of hydrogen peroxide |
| 3 | an aqueous mixture of equal volumes of solutions placed on discs 1 and 2 |
| 4 | an aqueous solution of povidone iodine containing ½ MBC concentration of iodine |
| 5 | an aqueous solution of hydrogen peroxide containing ½ MBC concentration of hydrogen peroxide |
| 6 | an aqueous mixture of equal volumes of solutions placed on discs 4 and 5 |

MBC - minimal bacterial concentration

A membrane with an established lawn of one of the following organisms indicated below in Table 1 was placed over the discs on one of the agar plates. In each case, the discs were exposed to the membrane for a period of 5 minutes to simulate the limited time of contact of the organism in the mouth with the oral lavage and the membrane was then removed from contact with the active agent discs and placed on one of a second series of nutrient agar plates to be incubated. Tetraphenyl tetrazolium chloride (TTC) was used as an indicator chemical to indicate viability. After 48 hours of incubation, the plates were observed to determine the bactericidal activity for each of the active agents for each of the concentrations on each disc and each plate.

Each of these tests was replicated 4 to 6 times except for the bacterium on Plate D on Table 1 below, which was replicated twice.

A fractional bactericidal concentration index was determined utilizing the technique to determine synergism disclosed by Elion et al., J. Biol. Chem., 208, 477-88 (1954) in accordance with the following formula:

$$\frac{(A)}{(MCB_A)} + \frac{(B)}{(MCB_B)} = \text{fractional bactericidal concentration} \leq 0.5$$

Where
A = the concentration of Agent A (PVP-$I_2$) in combination with Agent B which produces the MBC
B = the concentration of Agent B ($H_2O_2$) in combination with Agent A (PVP-$I_2$) which produces the MBC
$MBC_A$ and $MBC_B$ = Minimal bacterial concentrations of agents singly.

Similarly Kerry et al., J. Antimicrobial Agents and Chemotherapy, 1, 417-27 (1975) disclose the use of the same formula, but establish synergism at a value of 0.7 or less as adequate indication of synergism.

Table 1 shows the bacterium for each of the plates and the fractional bacterial concentration index for the novel oral lavage mixture of this invention against each of the six bacterium.

TABLE 1

| Ex. | Bacterium | Fractional Bactericidal Concentration Index |
|---|---|---|
| 2 | *Actinomyces viscosus* | 0.55 |
| 3 | *Actinobacillus actinomycetemcomatans* | 0.50 |
| 4 | *Bacteroides intermedius* | 0.50 |
| 5 | *Bacteroides gingivalis* | 0.62 |
| 6 | *Capnocytophaga ochracea* | 1.00 |
| 7 | *Fusobacterium nucleatum* | 1.00 |

As can be see from the Table, the novel oral lavage mixture of this invention is synergistic when applied to the bacterium of EXAMPLES 2-5 according to the teaching of Kerry et al and nearly synergistic when applied to the bacterium of EXAMPLES 6 and 7.

These tests clearly show the unexpected results obtained when mixing povidone iodine complex and hydrogen peroxide in accordance with this invention for use as an oral lavage in the treatment of four of the six bacterium that have been identified as being implicated in periodontal disease.

EXAMPLES 8-12

Five patients were treated with an oral lavage comprised of a 1:1 volume mixture of a 3% solution of hydrogen peroxide and a 10% solution of povidone iodine complex, in accordance with the following procedure.

The five patients having periodontal disease were treated by infusion of the gums in the office of a periodontist, and/or by frequent rinsing of the mouth with the oral lavage of this invention. Presented below in Table 2 is a count of the spirochetes found in the periodontal pockets of the patients over a one month period.

TABLE 2

THE EFFECT OF USING THE COMBINATION POVIDONE-IODINE AND HYDROGEN PEROXIDE ON SPIROCHETES FOUND IN THE PERIODONTAL POCKET

| | Number of Spirochetes Per Field | | | | |
|---|---|---|---|---|---|
| | Pre-Drug | Medication Phase | | | |
| Example | Day 1 | Day 8 | Day 22 | Day 31 | Comments |
| 8 | 100 | 12-15 | Not Done | 0-1 | Continued therapy 1 year - count then 0 to 1 |
| 9 | 30-50 | 50 | 2-5 | 4-9 | Continued therapy 1 year - count then 0 to 1 |
| 10 | 10 | 0-1 | 0-1 | 1-3 | Continued therapy 1 year - count then 0 (Not used during week) |
| 11 | 80-100 | 80 | 2-5 | Not Done | Dropped out one month after study began - gingival condition greatly improved |

TABLE 2-continued

THE EFFECT OF USING THE COMBINATION POVIDONE-IODINE AND HYDROGEN PEROXIDE ON SPIROCHETES FOUND IN THE PERIODONTAL POCKET

| | Number of Spirochetes Per Field | | | | |
|---|---|---|---|---|---|
| | Pre-Drug | Medication Phase | | | |
| Example | Day 1 | Day 8 | Day 22 | Day 31 | Comments |
| 12 | 10–25 | 20 | Not Done | Not Done | Dropped out due to improved gingival condition |

Table 2 shows that in all cases after a four week use of the oral lavage of this invention, the subgingival spirochete count was reduced, with patients maintaining a low reading while on the medication.

In some of the patients, treatment was continued for a one year period following the period referred to in the Table and the number of spirochetes continued to remain low.

These examples indicated that the method of applying the oral lavage of this invention unexpectedly provided marked alleviation of the periodontal disease of the patients.

EXAMPLES 13–15

Three series identified as EXAMPLES 13–15, respectively, were conducted to examine the bactericidal activity of multiple combinations of PVP-$I_2$ (povidone iodine complex) and $H_2O_2$ against three strains of bacteria shown previously to exhibit fractional bactericidal concentration (FBC) indices suggestive of synergistic reactions to the admixture of PVP-$I_2$ and $H_2O_2$. The bacterial strains tested were *Actinomyces viscosus* (ATCC #19246), *Bacteroides intermedius* (ATCC #33563) and *Bacteroides gingivalis* (ATCC #33277).

The method used to demonstrate synergy between PVP-$I_2$ and $H_2O_2$ was the checkerboard isobol design for mixing agents as described by Sabath (1968) and Caulfield and Wannemuehler (1982) and the determination of bactericidal endpoints using the membrane transfer technique described by Caulfield and Wannemuehler (1983). Each example involved testing at one time 24 different combinations of agents. To accomplish this, 142 mm agar plates and 10 cm×10 cm membrane filters were custom-made to accomplish this. The inoculum of bacteria used to "seed" the membrane was adjusted based on surface area of the larger membrane. Accordingly a 0.7 ml inoculum was used in this series of examples.

A stock solution of 30.0% $H_2O_2$ (Fisher Scientific, H-325) was diluted two-fold in sterile 3×distilled water just prior to each experiment to yield concentrations of 15.0%, 7.5%, 3.8%, and 1.9%.

The aqueous PVP-$I_2$ stock solution (10.0% PVP-$I_2$ solution, available $I_2$ 1.1%) was diluted two-fold in sterile 3×distilled water just prior to each experiment and placed in the front row of the multi-well dish.

From each dilution of the $H_2O_2$ and PVP-$I_2$, various combinations (60 total) of the admixture were prepared according to the MBC of the agents singly against each of the bacteria tested. Consequently, the maximum concentrations of PVP-$I_2$ and $H_2O_2$ for *B. gingivalis* and *B. intermedius* were 10.0% and 15.0%, respectively. The maximum concentrations of PVP-$I_2$ and $H_2O_2$ for *A. viscous* were 10.0% and 30.0%, respectively. The actual concentrations present on each disk are given in Tables 3 (*B. gingivalis* and *B. interedius*) and 4 (*A. viscous*). Note: concentrations of PVP-$I_2$ are given as percent $I_2$ in all Tables and Figures.

Sterile ¼" standardized paper filter disks were placed into wells containing agents singly and in combination. Each disk absorbed a maximum of 0.30 µl of agent(s). The disks were then placed onto a 142 mm blood agar plate in a 5×5 matrix pattern. Each experiment included a positive control disk saturated with 1.0% $I_2$-KI aqueous solution.

The square 10 cm×10 cm lawn containing membranes were then placed over the disks for a total exposure time of 5 minutes. The membranes were then removed and placed onto pre-reduced enriched Trypticase-soy blood medium (ETSA) containing tetrazolium indicator to denote viability. The plates were then immediately placed in an anaerobic chamber and incubated 24 hours. MBC endpoints were scored by two independent examiners. Isobolograms (FIGS. 1, 2, and 3) were constructed from the MBC endpoints given in Tables 5, 6, and 7. The experiment was repeated six times (duplicates×3) to yield the mode value for each MBC endpoint.

Figure 1:
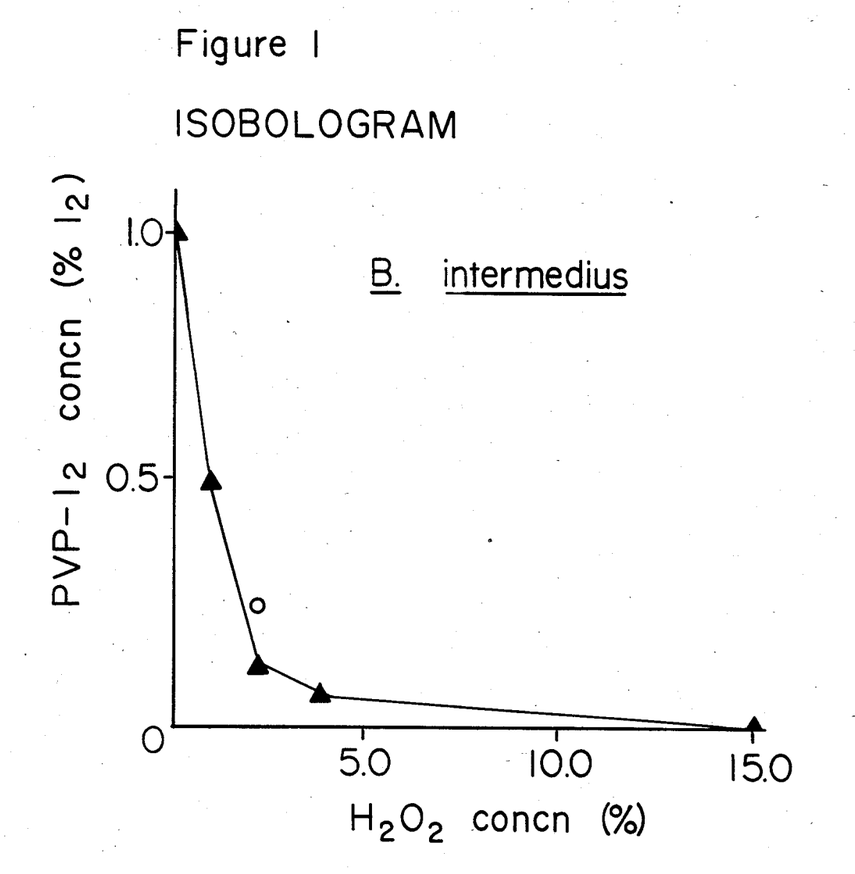
FIG. 1 diagrammatically illustrates antibacterial activity of the two antimicrobials against *B. intermedius;*
Figure 2:
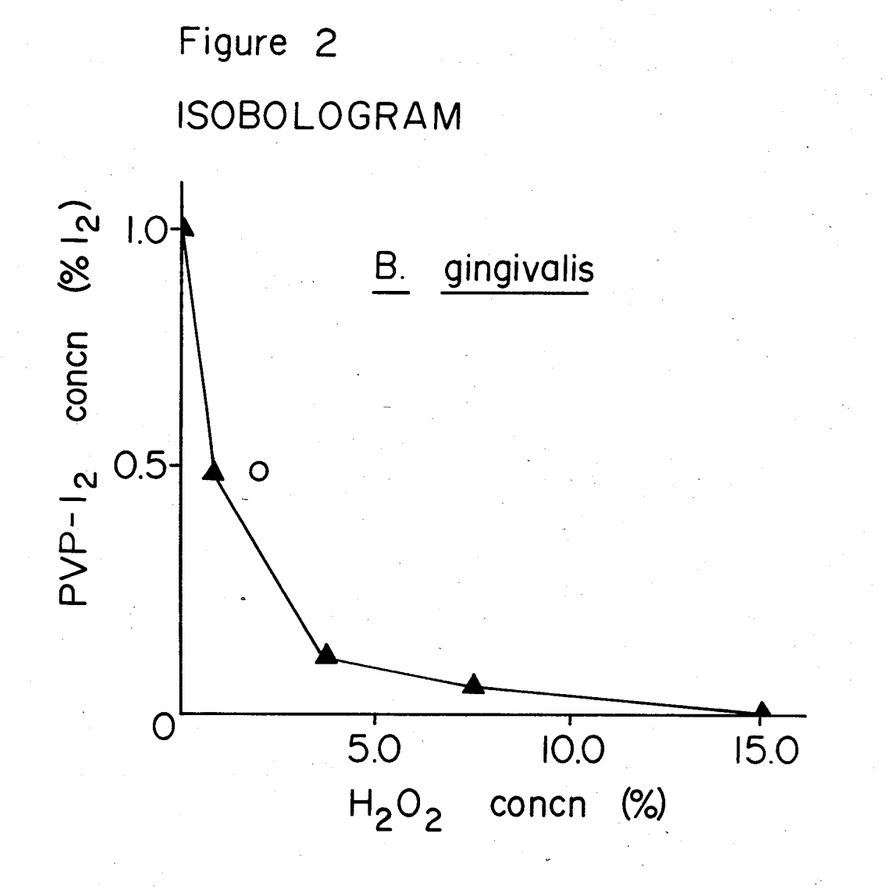
FIG. 2 diagrammatically illustrates antibacterial activity of the two antimicrobials against *B. gingivalis;*
Figure 3:
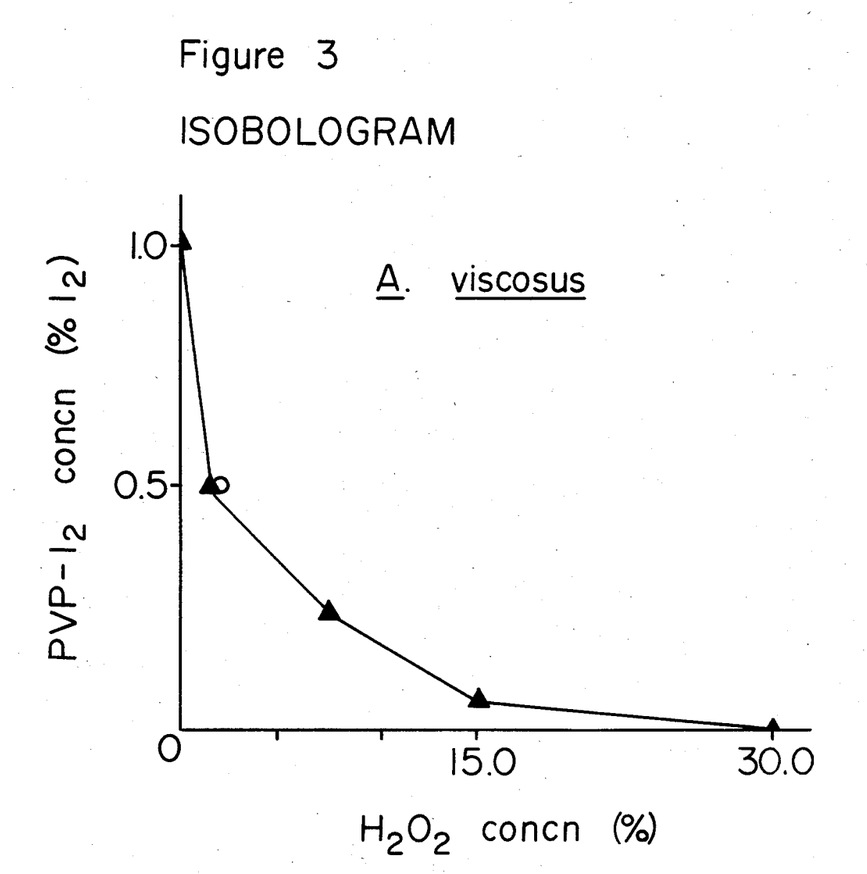
FIG. 3 diagrammatically illustrates antibacterial activity of the two antimicrobials against *A. viscosus;*

Results are given in tabular form in Tables 5, 6, and 7 and graphically as isobolograms in FIGS. 1, 2, and 3. Included are MBC endpoints of combinations of agents derived from a previous experiment. Agreement between these Examples and the previous experiment is evident.

Figure 4:
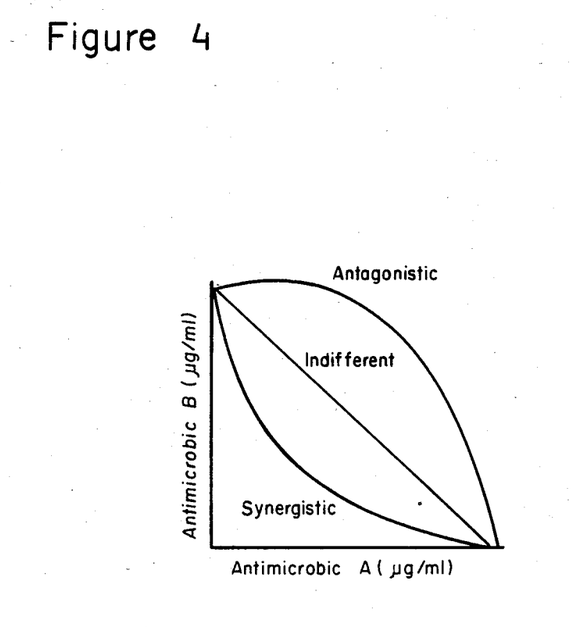
FIG. 4 diagrammatically illustrates the three possible results of testing the two antimicrobials singly and in combination.

FIG. 4 (from Sabath, 1968) shows the geometry of the isobologram for each of the possible outcomes for agent interactions. FIG. 4 is an isobologram portraying three possible results when two antimicrobics (A and B) are tested singly and in various combinations; either MIC or MLC endpoints may be plotted. A straight line joining the values obtained with each drug separately represented an isobol which indicates indifference. Antagonism is indicated by an isobol which bows upward away from the coorindates, and a bowing toward the coordinates indicates synergism. As can be seen from FIGS. 1, 2, and 3, the combination of PVP-$I_2$ and $H_2O_2$ clearly show synergistic bactericidal activity against all three bacteria tested when compared with FIG. 4.

These experiments together with the computation of the fractional bactericidal concentration indices (FBCs) from former experiments conclusively demonstrate synergistic interaction between PVP-$I_2$ and $H_2O_2$ against three periodontopathic bacteria, *A. viscous*, *B. intermedius*, and *B. gingivalis*.

Optimal combinations of PVP-$I_2$ and $H_2O_2$ can be selected from points on the line of the isobologram. Considerations such as ease of mixing, toxicity, stability of stock solutions, and spectrum of activity, among other considerations influence the selection of the appropriate admixture for clinical application for a given patient.

TABLE 3

Checkerboard Design for Determining MBCs of Various Combinations and Concentrations of PVP-$I_2$ and $H_2O_2$ Against *B. gingivalis* and *B. intermedius*

| $H_2O_2$ conc (%) | | PVP-$I_2$ concn. (% $I_2$) | | | |
|---|---|---|---|---|---|
| | $I_2$ control | 0.12 | 0.25 | 0.50 | 1.00 |
| 1.9 | | 0.06/1.0 | 0.12/1.0 | 0.25/1.0 | 0.50/1.0 |
| 3.8 | | 0.06/1.9 | 0.12/1.9 | 0.25/1.9 | 0.50/1.9 |
| 7.5 | | 0.06/3.8 | 0.12/3.8 | 0.25/3.8 | 0.50/3.8 |
| 15.0 | | 0.06/7.5 | 0.12/7.5 | 0.25/7.5 | 0.50/7.5 |

TABLE 4

Checkerboard Design for Determining MBCs of Various Combinations and Concentrations of PVP-$I_2$ and $H_2O_2$ Against *A. viscosus*

| $H_2O_2$ concn (%) | $I_2$ control | PVP-$I_2$ concn. (% $I_2$) | | | |
|---|---|---|---|---|---|
| | | 0.12 | 0.25 | 0.50 | 1.00 |
| 3.8 | | 0.06/1.9 | 0.12/1.9 | 0.25/1.9 | 0.50/1.9 |
| 7.5 | | 0.06/3.8 | 0.12/3.8 | 0.25/3.8 | 0.50/3.8 |
| 15.0% | | 0.06/7.5 | 0.12/7.5 | 0.25/7.5 | 0.50/7.5 |
| 30.0% | | 0.06/15.0 | 0.12/15.0 | 0.25/15.0 | 0.50/15.0 |

TABLE 5

Minimal Bactericidal Concentrations of PVP-$I_2$ and $H_2O_2$ Singly and in Combination Against *B. intermedius*

| MBCs* | |
|---|---|
| PVP-$I_2$ concn (% $I_2$) | $H_2O_2$ concn (%) |
| 1.0 | 0 |
| 0.5 | 1.0 |
| 0.25** | 3.8** |
| 0.12 | 1.9 |
| 0.06 | 3.8 |
| 0 | 15.0 |

*mode values of 6 determinations
**value from previous experiment

TABLE 6

Minimal Bactericidal Concentrations of PVP-$I_2$ and $H_2O_2$ Singly and in Combination Against *B. gingivalis*

| MBCs* | |
|---|---|
| PVP-$I_2$ concn (% $I_2$) | $H_2O_2$ concn (%) |
| 1.0 | 0 |
| 0.5 | 1.0 |
| 0.5** | 2.0** |
| 0.12 | 3.8 |
| 0.06 | 7.5 |
| 0 | 15.0 |

*mode values of 6 determinations
**value from previous experiment

TABLE 7

Minimal Bactericidal Concentrations of PVP-$I_2$ and $H_2O_2$ Singly and in Combination Against *A. viscosus*

| MBCs* | |
|---|---|
| PVP-$I_2$ concn (% $I_2$) | $H_2O_2$ concn (%) |
| 1.0 | 0 |
| 0.5 | 1.9 |
| 0.5** | 1.5** |
| 0.25 | 7.5 |
| 0.06 | 15.0 |
| 0 | 30.0 |

*mode values of 6 determinations
**value from previous experiment

EXAMPLE 16

A test program was conducted on human patients to determine the relative effect of the novel method of this invention utilizing an oral lavage for controlling and treating periodontal disease. A group of 68 patients who were susceptible to forming plaque and who had general gingivitis were divided into four cells of 17 patients each. Each cell was subjected to the following procedure:

Two vials each containing 10 ml of fluid assigned to the patients of each cell were mixed together to form a 20 ml solution. The patient then rinsed with the solution for a total of 30 seconds in two "swishes". The first "swish" of approximately 10 ml was used to wet the tissues thoroughly for approximately 7 to 10 seconds and then expectorated. The second "swish" of approximately 10 ml was used to rinse the teeth and gums for the balance of the 30 seconds and then expectorated. Each individual used a total of 9 rinsing treatments on Monday, Wednesday, and Friday over a three week period. In the interim, a non-fluoridecontaining toothpaste with a soft bristled toothbrush was used as the only means to clean the teeth. The following fluids were used as an oral lavage for patients in each cell:

| Cell | Vial 1 | Vial 2 |
|---|---|---|
| 1 | water | water |
| 2 | povidone iodine (1.0% $I_2$) | hydrogen peroxide (3%) |
| 3 | water | povidone iodine (1.0% $I_2$) |
| 4 | water | hydrogen peroxide (3%) |

In the treatment of patients in Cells 2 and 3, when Vial 1 and Vial 2 were admixed, the resulting concentration of iodine was 0.5 percent. In the treatment of Cells 2 and 4, when Vial 1 and Vial 2 were admixed, the resulting concentration of hydrogen peroxide was 1.5 percent.

Each patient was evaluated for plaque accumulation and gingivitis by standard procedures immediately before the first rinse and immediately after the ninth rinse.

A total base line score was established for gingivitis and plaque accumulation for each cell of patients at the beginning of the test. After the three week period of treatment, it was determined that the mean percent decrease in gingivitis and plaque accumulation from the base line by cell was as follows:

| Cell | Mean % Decrease |
|---|---|
| *Gingivitis* | |
| 1 | 15.6 |
| 2 | 24.8 |
| 3 | 12.1 |
| 4 | 16.8 |
| *Plaque Accumulation* | |
| 1 | 11.2 |
| 2 | 23.3 |
| 3 | 21.7 |
| 4 | 6.3 |

Although a relatively small number of patients were used, the results were encouraging. The data, within the limitations of the study design, indicates an additive effect when povidone iodine and hydrogen peroxide are combined for the treatment of symptons and signs of periodontal disease. However, evidence of synergism was absent in this test. This result is not surprising, however, because the use in humans of combinations of individually effective pharmaceutical agents rarely demonstrates synergism.

What is claimed is:

1. A method of treating teeth in a human oral cavity to retard or reduce the formation of plaque thereon which comprises applying to the teeth and to plaque thereon an antimicrobial oral lavage in the form of an aqueous solution containing from about 0.5 to about 10.0% by weight of hydrogen peroxide and from 0.05 to about 2.0% by weight of iodine derived from a povidone-iodine complex in an amount and for a period of time sufficient to exert cidal action on microorganisms in or constituting said plaque and thereafter expelling the oral lavage from the oral cavity.

2. A method according to claim 1 wherein the antimicrobial oral lavage is applied for a period of time of the order of 20 to 40 seconds.

3. A method according to claim 1 wherein the weight ratio of hydrogen peroxide to derived iodine ranges from about 0.25:1 to about 200:1.

4. A method according to claim 1 wherein the weight ratio of hydrogen peroxide to derived iodine ranges from about 2:1 to about 40:1.

5. A method according to claim 1 wherein the antimicrobial oral lavage exerts its cidal action against *Actinomyces viscosus, Bacteroides intermedius* and *Bacteroides gingivalis* present in the oral cavity.

6. A method according to claim 5 wherein the cidal action against the bacteria is carried out by swishing it in the oral cavity.

7. A method according to claim 6 wherein the cidal action is carried out by a plurality of swishes, each swish being expectorated prior to the application of the succeeding swish.

8. A method according to claim 7 wherein each swish wets both the teeth and the gum structure in the oral cavity.

9. A method according to claim 1 wherein the application of the oral lavage is carried out by rinsing.

10. A method according to claim 8 wherein the application of the oral lavage is carried out by infusion.

11. A method according to claim 10 wherein the infusion washes and debrides the teeth and gums.

12. A method of prolonging the healthy condition of teeth and gums of the human oral cavity against the accumulation of plaque on the teeth and the detrimental effects of such plaque on the teeth which comprises subjecting the teeth to the wetting action of an oral lavage having a cidal action against plaque-forming bacteria in the oral cavity and which oral lavage is in the form of an aqueous alcoholic solution containing from about 0.5 to about 10% by weight of hydrogen peroxide and from about 0.05 to about 2.0% of iodine derived from a povidone-iodine complex.

13. A method according to claim 12 wherein the aqueous alcoholic oral lavage solution is freshly prepared just prior to use.

* * * * *